(12) United States Patent
Rowlandson

(10) Patent No.: US 6,665,559 B2
(45) Date of Patent: Dec. 16, 2003

(54) METHOD AND APPARATUS FOR PERIOPERATIVE ASSESSMENT OF CARDIOVASCULAR RISK

(75) Inventor: G. Ian Rowlandson, Milwaukee, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 334 days.

(21) Appl. No.: 09/752,081

(22) Filed: Dec. 29, 2000

(65) Prior Publication Data

US 2002/0042579 A1 Apr. 11, 2002

Related U.S. Application Data

(63) Continuation-in-part of application No. 09/684,064, filed on Oct. 6, 2000.

(51) Int. Cl.[7] ............................................. A61B 5/04
(52) U.S. Cl. ...................................... 600/515; 600/513
(58) Field of Search ................................ 600/515, 508, 600/513, 518

(56) References Cited

U.S. PATENT DOCUMENTS

| | | |
|---|---|---|
| 4,957,115 A | 9/1990 | Selker |
| 4,998,535 A | 3/1991 | Selker et al. |
| 5,276,612 A | 1/1994 | Selker |
| 5,277,188 A | 1/1994 | Selker |
| 5,501,229 A * | 3/1996 | Selker et al. ............... 600/508 |
| 5,718,233 A | 2/1998 | Selker et al. |
| 5,724,983 A | 3/1998 | Selker et al. |
| 6,049,730 A | 4/2000 | Kristbjarnarson |
| 6,067,466 A | 5/2000 | Selker et al. |
| 6,230,048 B1 | 5/2001 | Selvester et al. |
| 6,339,720 B1 * | 1/2002 | Anzellini et al. ............ 600/517 |

* cited by examiner

*Primary Examiner*—Angela D. Sykes
*Assistant Examiner*—Roderick Bradford
(74) *Attorney, Agent, or Firm*—Michael Best & Friedrich LLP

(57) ABSTRACT

A method and apparatus for providing real-time support in interpreting a patient's ECG in order to assess the probability of perioperative cardiovascular risk associated with performing a non-cardiac surgery. The apparatus includes an acquisition unit for acquiring an ECG and a processor for determining whether the ECG has diagnostic statements of risk. From the diagnostic statements of risk, the processor determines the probability of cardiovascular risk associated with the non-cardiac surgery. The probability of cardiovascular risk is displayed on display in the form of an indicator of either major, intermediate, or minor cardiovascular risk.

The method includes acquiring a patient's ECG, determining whether the ECG exhibits diagnostic statements of cardiovascular risk, and determining the probability of cardiovascular risk based on the diagnostic statements, and displaying the determined probability of cardiovascular risk.

17 Claims, 9 Drawing Sheets

Fig. 1

010566  04/23/1992  07:39:36  JOHN DOE  66kg  BP:160/95
          56 years  Male Dx: Chest pain chief complnt Rate    58
PR     158
QRSD    91
QT     415
Qtc    408

- - AXIS - -
P       28
QRS    -37
        94

- ACI-TIPI PREDICTED PROBABILITY OF ACUTE CARDIAC ISCHEMIA - 42%, based on:
  - - - Patient is male, age greater than 50
  - - - Patient has chief complaint of chest pain/discomfort or left arm pain
  - - - No significant Q waves or primary ST segment abnormalities detected
  - - - Anterior T waves flat or slightly inverted in two or more of leads V1 - V4
- ACI-TIPI PROBABILITY MAY ASSIST PHYSICIAN TRIAGE JUDGEMENT (1.0111 5.1100 9.0050)

Reason Statements

METHOD AND APPARATUS FOR PERIOPERATIVE ASSESSMENT OF CARDIOVASCULAR RISK

RELATED APPLICATIONS

This application is a continuation-in-part of U.S. patent application Ser. No. 09/684,064.

BACKGROUND OF THE INVENTION

Physiological activity is monitored in the diagnosis and treatment of numerous diseases and medical conditions. For example, heart activity is commonly monitored by collecting electrocardiographic ("ECG") data. ECG data is typically interpreted by a cardiologist, a physician specially trained in reading the waveforms created by ECG equipment.

In many situations, ECG and other physiological data is available, but an expert suitably trained in reading that data is not. In response to this problem, software interpretation tools have been developed to aid the non-expert physician in interpreting and using such data. However, these tools, particularly ECG tools, are not satisfactory. Existing ECG tools are designed to generate an interpretation. The computer-generated interpretation may be supported by one or more statements that describe the criteria that the computer uses to reach its conclusion. However, these statements are typically limited to describing the character of the waveform, which is usually of little assistance to the novice ECG reader. Another shortcoming of existing tools is that they generate conclusions based on the assumption that the ECG device correctly measured the ECG. In other words, existing computer tools assume that no faults or other errors ever occur in ECG measuring equipment.

The output from an existing ECG interpretation system is shown in FIG. 1. The output includes a screen image 10. The image 10 includes patient identifying information 12, initial diagnostic information 14, such as a complaint or symptom, measurements 16, physiological data in the form of waveforms 18, a diagnosis or interpretation 22, and a group of reason statements 24. In the example shown, the interpretation 22 indicates that there is a 42% probability that the patient has acute cardiac ischemia. The reasons supporting the interpretation are set out in the reason statements 24. For example, the interpretation is based on the fact that the patient is male, complaining of chest pain, and that "no significant Q waves or primary ST segment abnormalities" were detected. The reason statements 24 also indicate that the "[a]nterior T waves" are flat.

Most non-specialists find reason statements such as those shown in FIG. 1 to be too technical and, therefore, unhelpful in understanding the interpretation. Further, non-specialists are generally uncomfortable relying on an interpretation lacking a high probability. In the example shown, the interpretation generated has a probability of only 42%, meaning that there is a 58% chance that another interpretation is appropriate for the data. Thus, in those cases where present systems generate an interpretation of equivocal probability, they are often of little help.

Moreover, in cases where a patient is about to undergo a non-cardiac surgery, there is a need to be able to accurately assess the perioperative cardiovascular risk to the patient of performing the surgery. Again, having to wait for a cardiologist to make such an assessment may not be practical or even possible.

SUMMARY OF THE INVENTION

Accordingly, the invention provides real-time support in interpreting a patient's ECG in order to assess the perioperative cardiovascular risk associated with performing a non-cardiac surgery. An acquisition unit acquires the patient's ECG. A processor, coupled to the acquisition unit, determines whether the acquired ECG has diagnostic statements of cardiovascular risk. From the diagnostic statements, the processor determines the probability of cardiovascular risk associated with the non-cardiac surgery. The probability of cardiovascular risk is then displayed to a clinician in the form of an indicator of either major, intermediate, or minor cardiovascular risk.

The invention also provides a new method of interpreting a patient's ECG in order to assess the perioperative cardiovascular risk associated with performing a non-cardiac surgery. The method includes acquiring a patient's ECG, determining whether the ECG exhibits diagnostic statements of cardiovascular risk, and determining the probability of cardiovascular risk based on the diagnostic statements. The method also includes displaying the determined probability of cardiovascular risk to a clinician in the form of an indicator of either major, intermediate, or minor cardiovascular risk.

BRIEF DESCRIPTION OF THE DRAWINGS

In the drawings:

FIG. 1 is an illustration of output from an existing physiological data interpretation system.

DETAILED DESCRIPTION

Before one embodiment of the invention is explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including" and "comprising" and variations thereof herein is meant to encompass the items listed thereafter and equivalents thereof as well as additional items.

Figure 2:
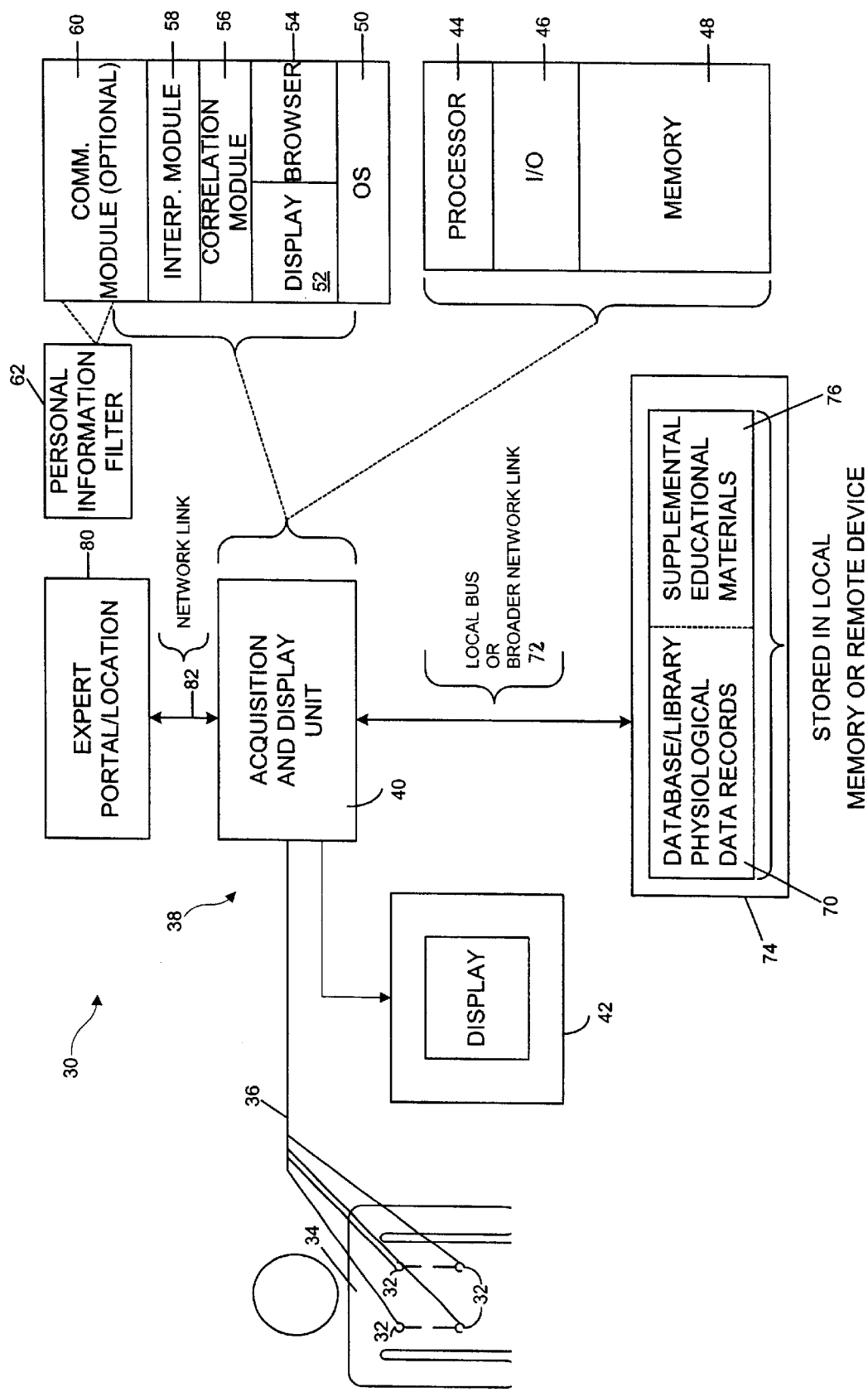
FIG. 2 is an illustration of a physiological interpretation system of the invention.

A physiological data system 30 is shown in FIG. 2. Before describing the system 30, it should be understood that the invention will be described with respect to ECG data. However, the system could be configured to aid in the interpretation of other data such as image data, including x-ray images, nuclear images, ultrasonic images, and magnetic resonance; blood pressure; oxygenation; brain activity;

etc. Thus, the invention should not be limited to the examples described and shown.

The system includes a number of sensors or similar devices 32 attached to a patient 34. Physiological data sensed by the sensors 32 is transmitted over a link 36 to an acquisition and display unit 38 having a main unit 40 and a display 42. The main unit 40 includes typical hardware such as a processor 44, an input/output interface 46, and data storage or memory 48. The main unit also includes an operating system 50 and other software in the form of a display module 52, an optional browser 54, such as a web browser, a correlation module 56, which may include an optional data integrity checking module (not shown), and an interpretation module 58.

Figure 5:
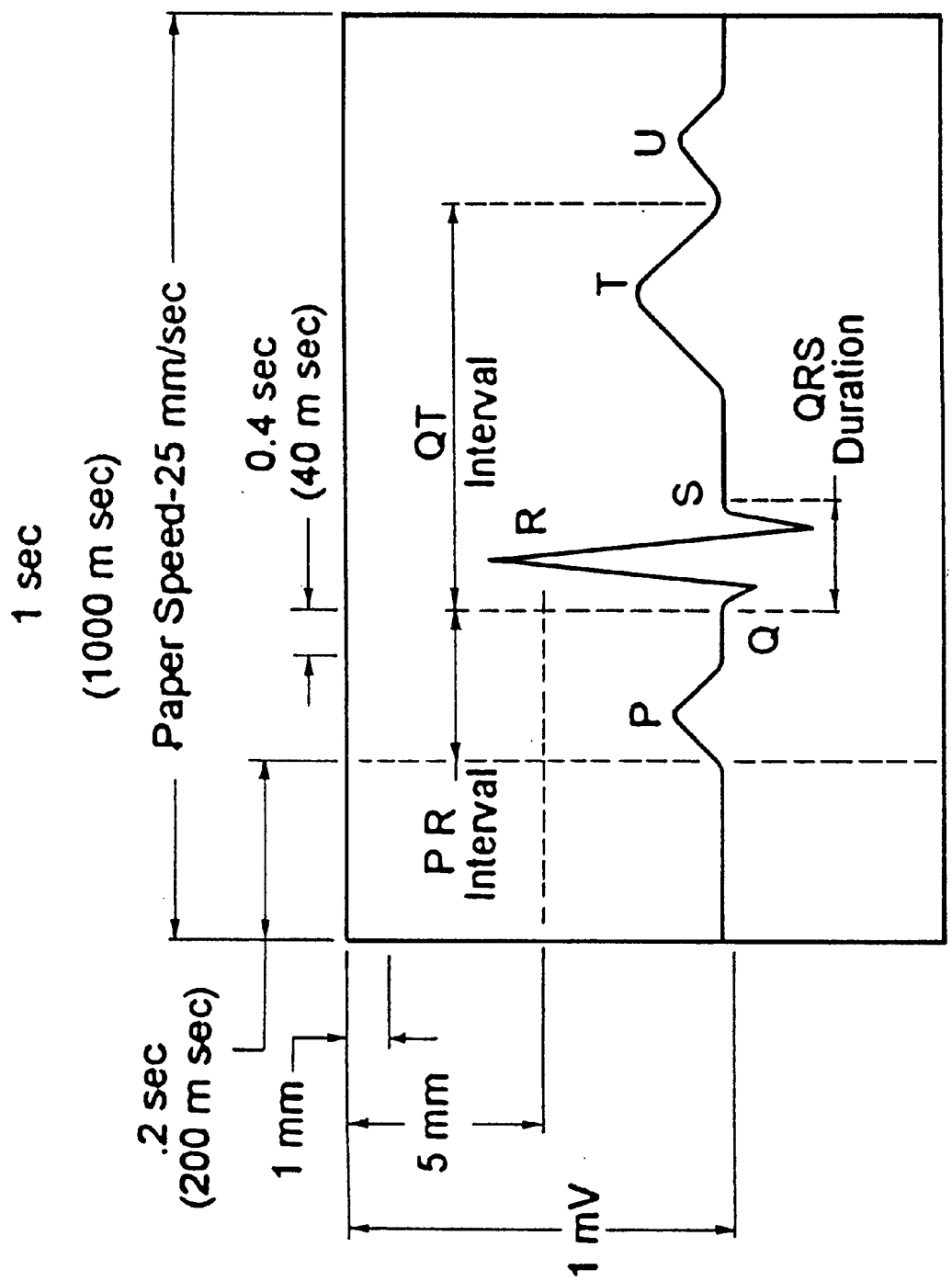
FIG. 5 is an illustration of measurements of physiological waveforms that are used to define features.

The acquisition and display unit 38 performs several functions. First, it acquires signals or raw data from the patient 34 using the sensors 32. The raw data is then measured. For example, and as shown in FIG. 5, when ECG data is acquired, numerous characteristics such as waveform height, distance between peaks, etc. are measured. Once the measurements are made, various features of the waveform are extracted. As will be discussed further below, these features can then be compared to the features of previously interpreted physiological data and used to check the interpretation made by the interpretation module 58.

The interpretation module 58 uses the measured features to generate an interpretation of the physiological data. A variety of existing physiological interpretation modules may be used in the invention. When configured to interpret ECG data, 12SL™ software available from GE Medical Systems Information Technologies, Inc. may be used in the invention.

The acquisition and display unit 38 may include an optional communication module 60 to coordinate and control communications with an expert location (discussed below) and remote libraries of data (also discussed below). Communications between the acquisition and display unit 38 and remote devices may be enhanced with an information filter 62 coupled to or made a part of the communication module 60. The information filter 62 may be configured to block the transmission of predetermined information, such as personal or private patient information, to ensure that the predetermined information is not transmitted to devices and locations coupled to the acquisition and display unit 38.

As noted, the interpretation module 58 analyzes and interprets the data or data set acquired from the patient 34, and generates an interpretation for that data set. The correlation module 56 then links the interpretation to physiological records that have the same or similar features and interpretation. For example, an anterior myocardial infarction (MI) that was elicited due to a poor R wave progression would be linked to ECGs with the same feature, as opposed to all ECGs that exhibit features that are possible with anterior MI.

The correlation module 56 links the interpretation to records in a library of physiological data records 70. Specifically, the correlation module 56 matches or correlates features extracted from the current physiological data to features in the previously interpreted records of physiological data stored in the library 70. The correlation module 56 then creates links, such as hyperlinks to the correlating records. The library of physiological data records 70 is coupled to the acquisition and display unit 38 via a communication link 72. The communication link 72 may be a local bus when the library of records 70 is stored in local storage or may be a variety of other links, including an Internet link, such that the library of records 70 may be stored on a remote server 74, which may be a web server. The server 74 may also include a library of additional or supplemental educational materials or information records 76 that can be linked to the displayed physiological data and correlated records to provide explanations of relevant features and characteristics of the data and interpretation. Locating the records 70 and 76 on a server has several advantages including the ability to maintain a central, easily updated depository of information. However, the records 70 and 76 could be maintained on separate servers or locally on the data acquisition and display unit 38.

The data and acquisition unit 38 may also be linked to an expert location 80 via a link 82. The expert location 80 may be a customized web site or portal and the link 82 may be an Internet link. However a variety of locations and communication links could be used. For example, a remote server with a dial-up link could be used in the invention. Communications between the expert location 80 and the data acquisition and display unit 38 may take place using text or voice-based electronic mail, instant messaging, or chat services. Such services are particularly suitable when the data acquisition and display unit 38 is configured such that the display module 52 directs physiological data images to be displayed in a window generated by the browser 54 and the expert location 80 is coupled to the unit 38 via an Internet connection.

The expert location 80 is a site or similar locale with a computer or similar appliance. Typical examples include a computer at an office or facility of an expert in the medical area relevant to the type of physiological data being interpreted by the interpretation module 58. Messages from the data acquisition unit 38 are received at the expert location 80 and responded to by the expert to assist the physician or other individual using the unit 38 to interpret the physiological data.

Figure 3:
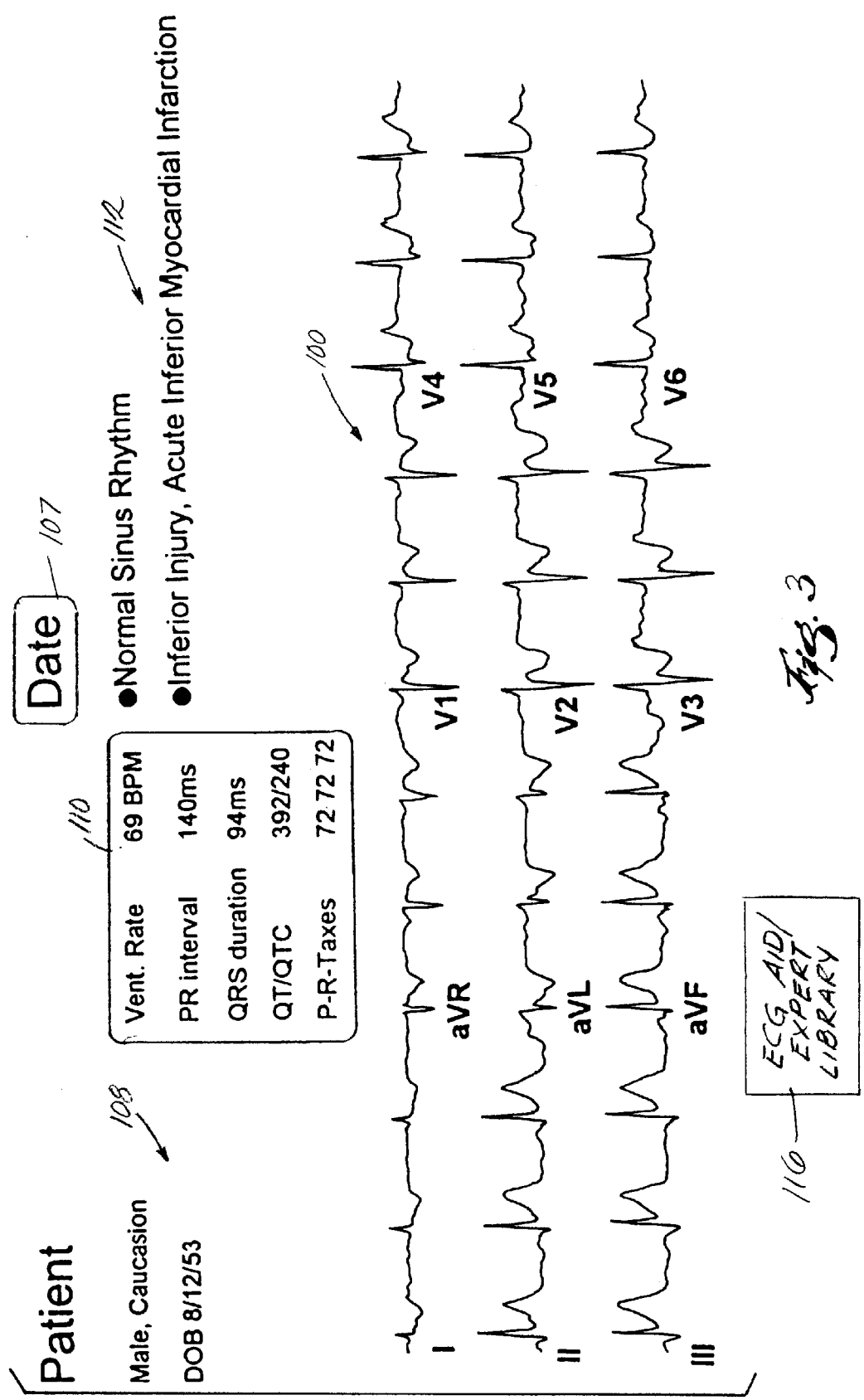
FIG. 3 is an illustration of output from the system of FIG. 2.

FIG. 3 illustrates physiological data in the form of an ECG 100. The ECG 100 also includes patient ECG identifying information 107, patient identifying information 108, measurements 110, and an interpretation 112. The interpretation 112 is generated by the interpretation module 58. Once the interpretation 112 is generated, the correlation module 56 reviews the library of records 70, determines matching physiological records, and links those matching records to the ECG record 100. The system 30 can be configured such that the selection of icon or button 116 in the browser 54 causes the display of the matching records.

Figure 4:
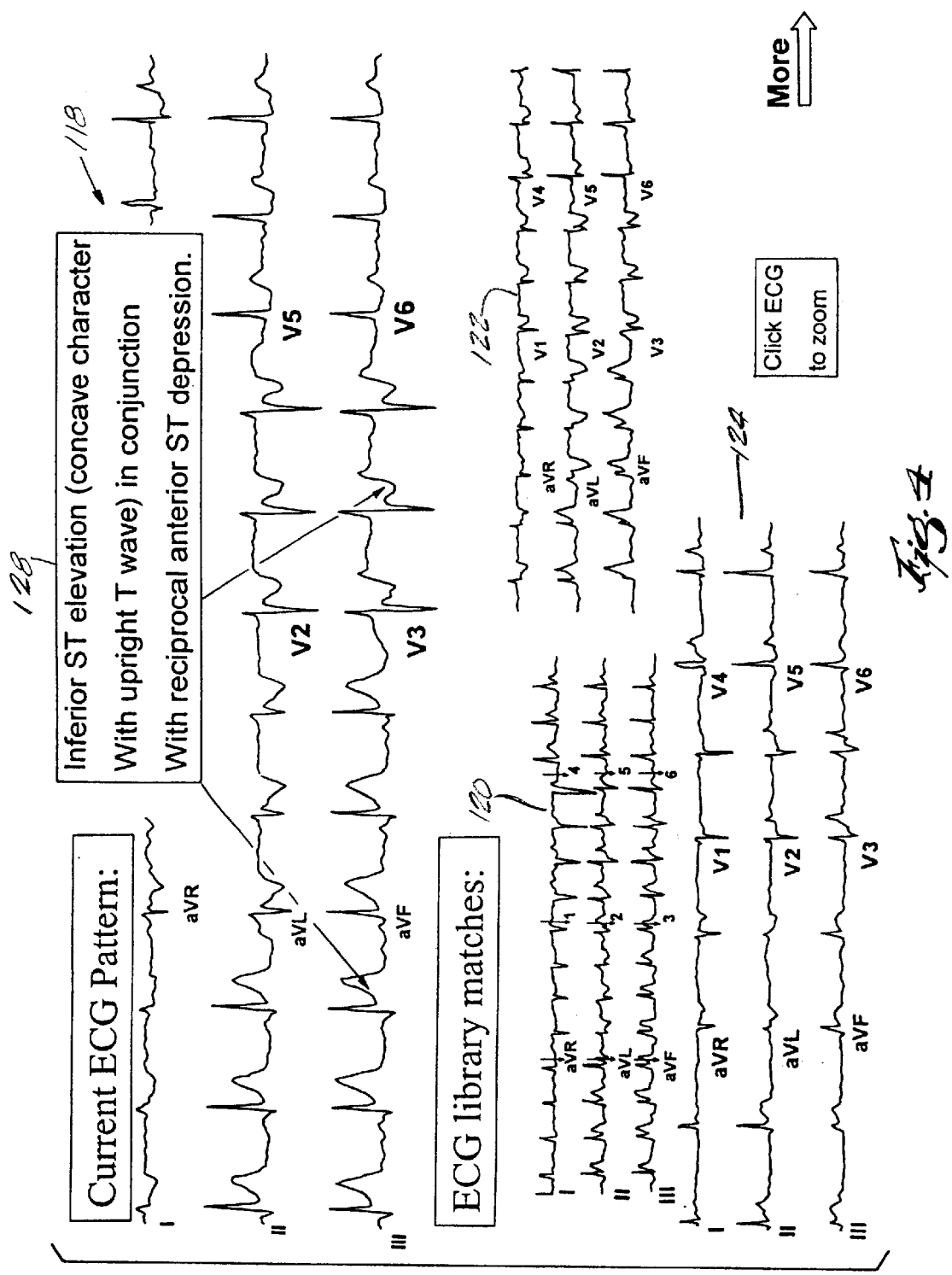
FIG. 4 is an illustration of output from the system of FIG. 2.

FIG. 4 shows a screen 118 including the ECG 100 with matching records 120, 122, and 124. The screen 118 also includes an explanatory statement 128 describing pertinent characteristics of the waveform.

In addition to providing an interpretation and supplemental information in the form of matching physiological records and explanatory statements, the invention may provide integrity checking. Preferably, the integrity checking is performed by the clinician once the matching physiological records and explanatory statements are displayed. The clinician detects any deviations between the acquired ECG and the physiological records that have been correlated to the acquired ECG from the library of physiological data records 70. Alternatively, the data acquisition and display unit 38 may include an integrity checking module (not shown) that ensures that the measurements made by the data acquisition and display unit 38 are not biased or erroneous due to faults or other problems in the unit 38.

Figure 6:
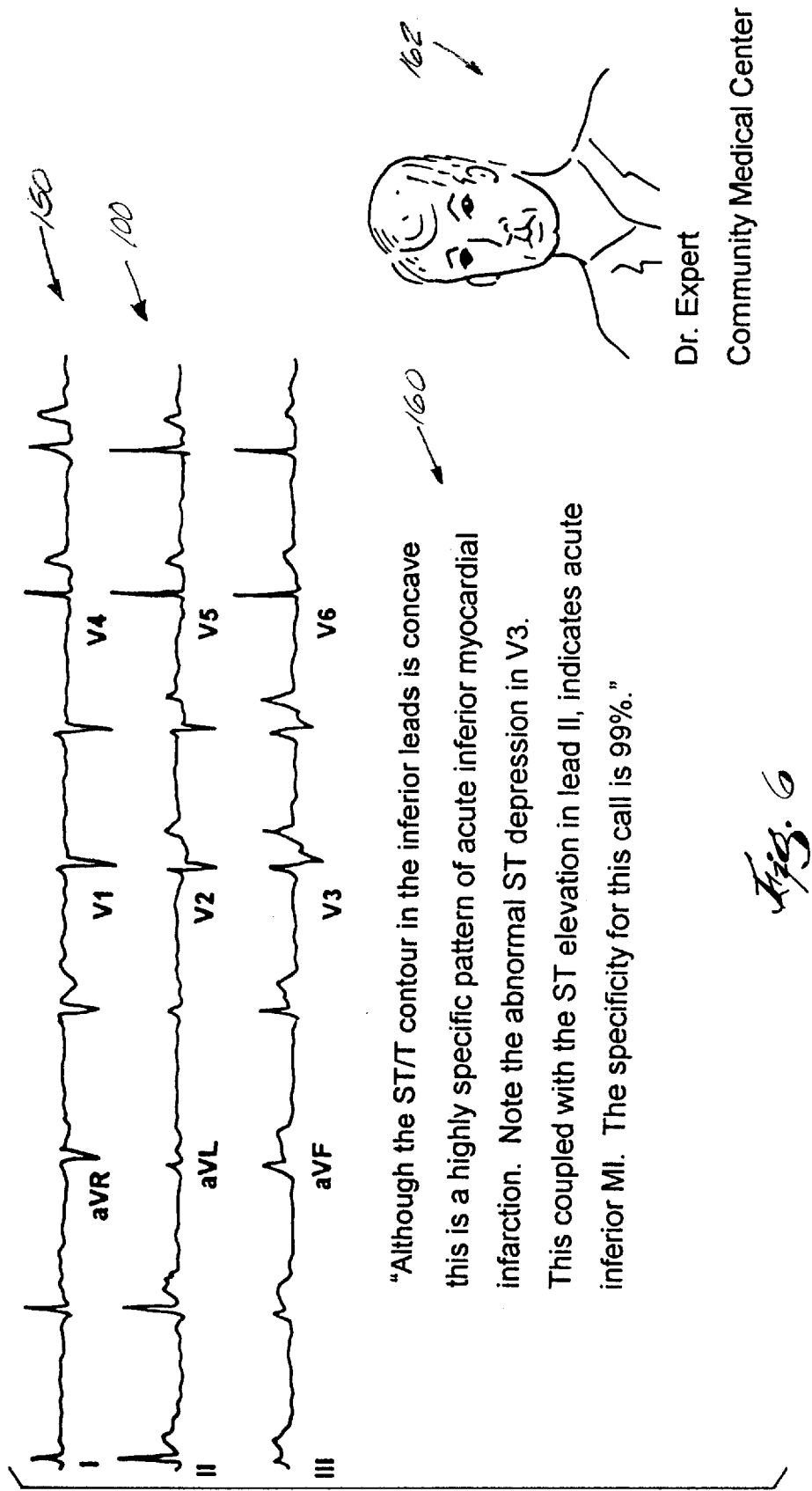
FIG. 6 is an illustration of a communication from an expert.

As noted above, if a system user desires additional information concerning the interpretation of the physiological data, he or she may obtain expert advice by communicating with the library of physiological data records 70 or an expert at the expert location 80. FIG. 6 shows an exemplary expert response screen 150 that may be displayed on the acquisition and display unit 38. The screen includes the ECG 100 with an expert commentary 160 that may be generated using one of the communication tools noted above. The expert response screen 150 may also include expert identifying information 162 such as the name and picture of the expert providing the commentary.

Figure 7:
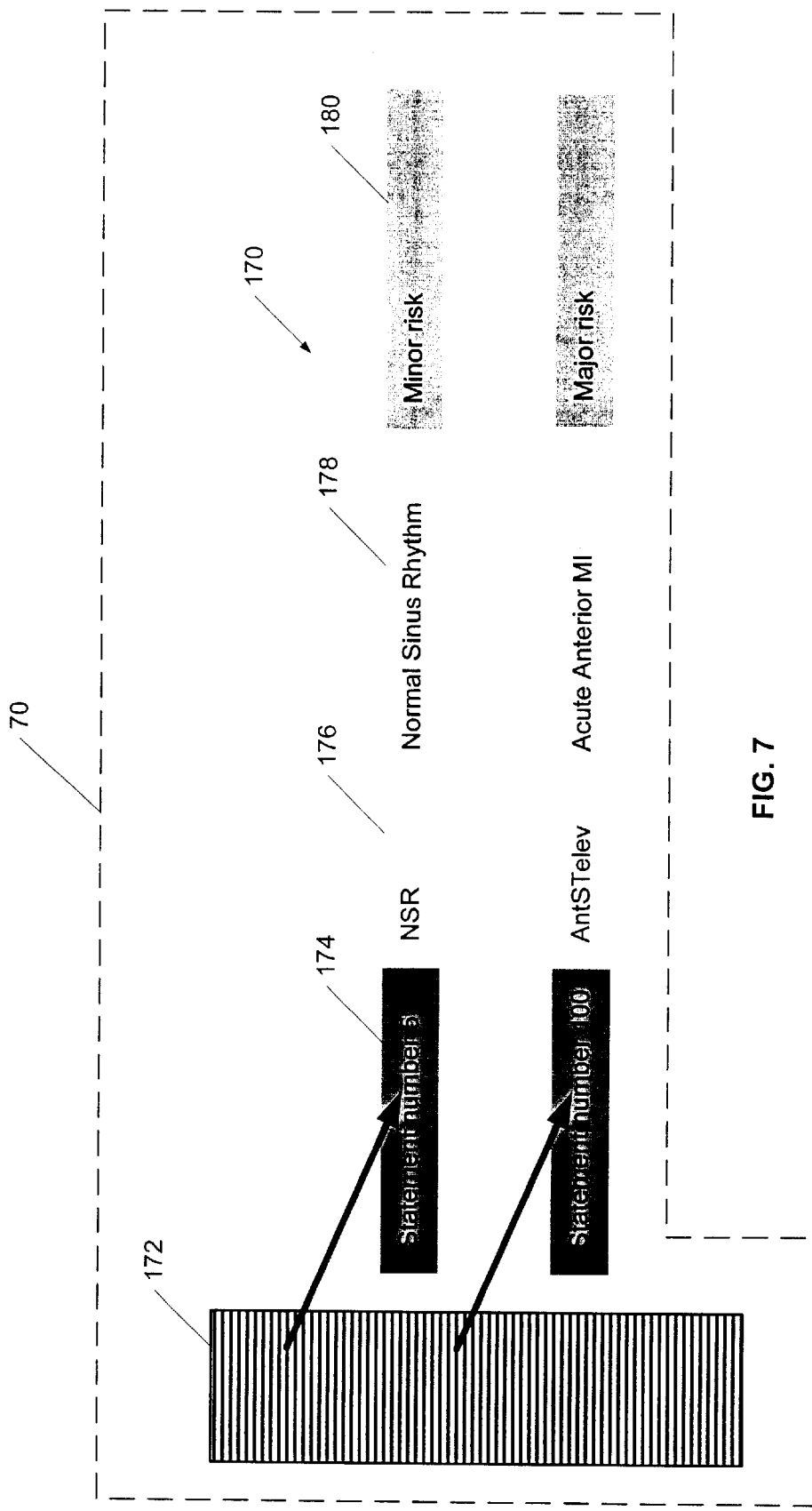
FIG. 7 is an illustration of a statement code for use in the method of the invention.
Figure 8:
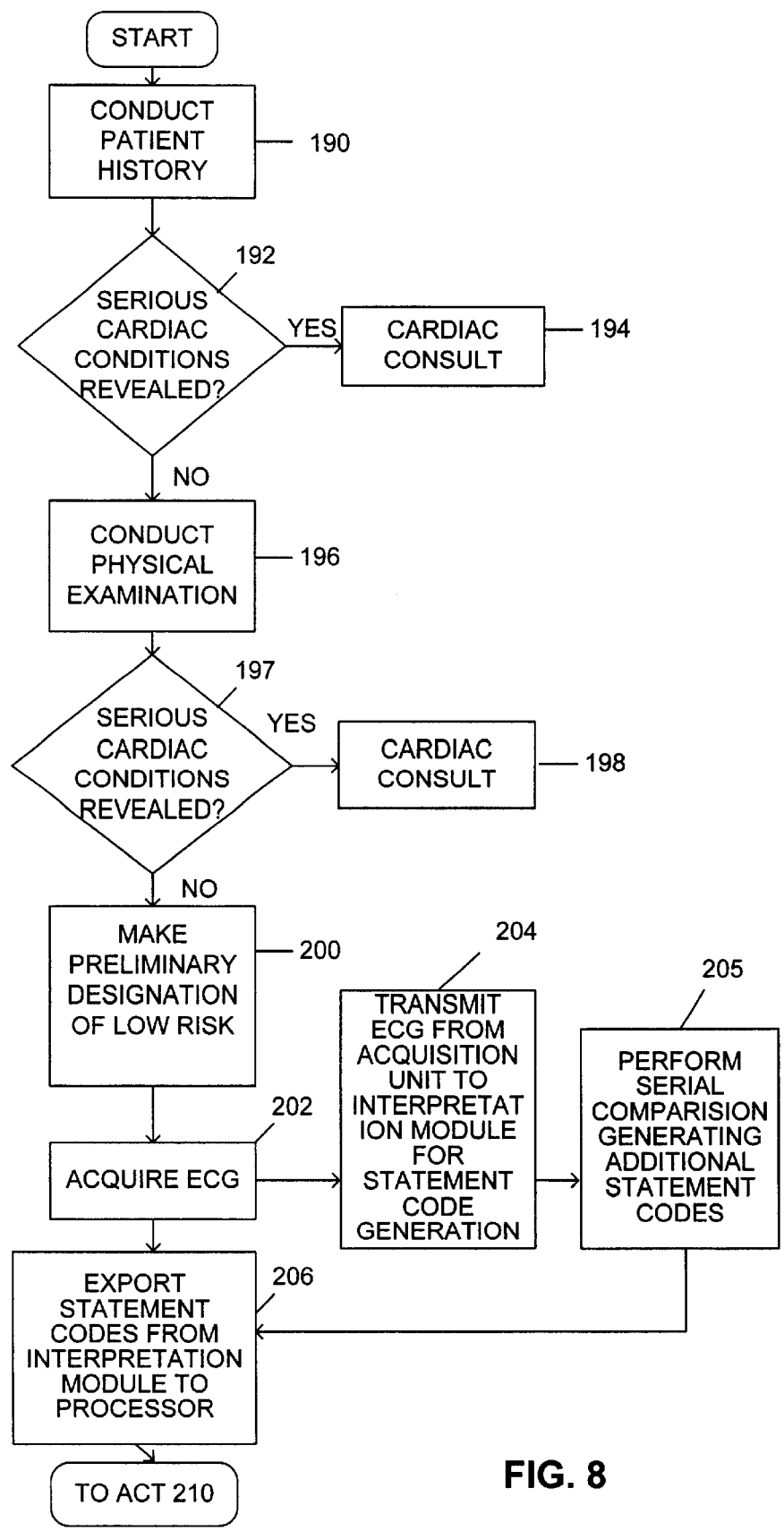
FIG. 8 is a flow chart illustrating the method of the invention.
Figure 9:
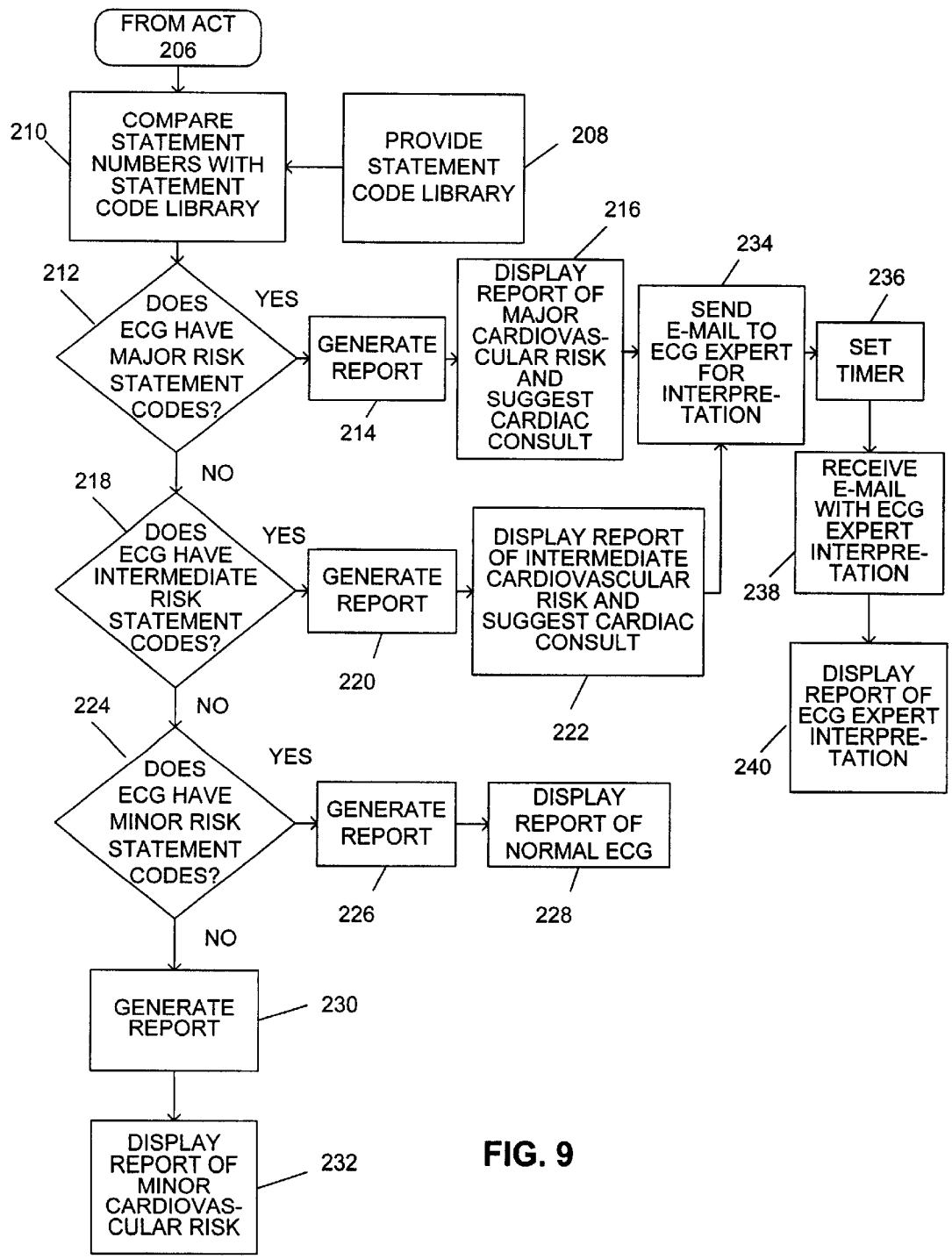
FIG. 9 is a flow chart continuing from FIG. 8 to further illustrate the method of the invention.

FIGS. 7, 8, and 9 illustrate a particular embodiment of the invention which is also useful for determining the perioperative cardiovascular risk to the patient of performing non-cardiac surgery on the patient. Like parts are identified using like reference numerals. This description incorporates by reference the subject matter of copending U.S. patent application Ser. No. 09/684,064.

Referring to FIGS. 2 and 7, the library of physiological data records 70 includes a statement code library 172. The statement code library 172 includes a plurality of statement codes 170 which are used to characterize ECG waveforms.

FIG. 7 illustrates two examples of statement codes 170. The statement codes 170 include a statement number 174, a statement acronym 176, a diagnostic statement 178, and a probability of perioperative cardiovascular risk 180. By way of example only, the statement code used to characterize an ECG exhibiting a normal sinus rhythm could include a statement number—5, an acronym—NSR, a diagnostic statement—Normal Sinus Rhythm, and a probability of cardiovascular risk—Minor risk.

In the most preferred embodiment, the statement codes 170 are configurable for clinical settings other than perioperative assessment of cardiovascular risk. Specifically, the probability of cardiovascular risk 180 can be configured to reflect the particular needs of different clinical settings. By way of example only, the statement codes 170 could be configured for cardiovascular screening in a family practice setting or in an emergency room setting.

When an ECG is acquired by the acquisition unit 40, the acquisition unit 40 inputs the ECG into the interpretation module 58 for analysis. Other inputs into the interpretation module 58 could include the type of non-cardiac surgery being performed, the amount of patient fluid being exchanged, or the specific components of the circulatory system that will be affected by the non-cardiac surgery. The interpretation module 58 analyzes the ECG, along with any other inputs, and assigns only statement numbers 174 to the ECG.

In order to assign the ECG with statement numbers 174, the interpretation module 58 analyzes the ECG as described below. Before the preferred embodiment of ECG analysis is described, it should be understood that any analysis of an acquired ECG in order to determine diagnostic statements associated with different levels of cardiovascular risk is within the scope of the present invention. It should also be understood that the diagnostic statements of cardiovascular risk discussed below are used merely as examples and do not limit the scope of the present invention. Moreover, the diagnostic statements implemented in the method of the invention may be more specific as to the particular cardiovascular event or condition than the diagnostic statements provided as examples below.

The interpretation module 58 first analyzes the ECG for any acute coronary syndromes which is associated with major cardiovascular risk. If the interpretation module 58 detects any acute coronary syndromes, the interpretation module 58 assigns a statement number 174 to the ECG designating the diagnostic statement of risk 178 and a probability 180 of major cardiovascular risk.

The term acute coronary syndrome is a broad term encompassing many different diagnostic statements, including acute myocardial infarction, injury, and acute ischemia. These diagnostic statements of major cardiovascular risk and the methods used by the interpretation module 58 to detect them are described below.

Acute myocardial infarction (MI) often includes three ECG characteristics, namely ischemia, injury, and Q-wave infarction, but any of the three characteristics may occur alone.

Ischemia is characterized by inverted T waves. Thus, if the interpretation module 58 detects an inverted T wave, the interpretation module 58 assigns the ECG a statement number 174 designating ischemia.

Injury is characterized by ST segment elevation, and ST segment elevation indicates that the MI is acute. Accordingly, if the ECG exhibits ST segment elevation, the interpretation module 58 assigns the ECG a statement number 174 designating acute MI. Preferably, the interpretation module 58 is capable of recognizing ECGs with even more specific diagnostic statements of cardiovascular risk. For example, the interpretation module 58 is capable of recognizing ECGs with ST segment elevations of a certain character, not just ST segment elevations generally.

The third ECG characteristic associated with acute infarction is the presence of a Q wave, referred to as Q-wave infarction. Q-wave infarction, especially with evidence of an acute change, is considered a clinical predictor of major cardiovascular risk. Thus, if the interpretation module 58 detects ST elevation concordant with the presence of a Q wave, the interpretation module 58 assigns the ECG a statement number 174 designating acute myocardial infarction.

A second category of diagnostic statements associated with major cardiovascular risk during non-cardiac surgery is arrhythmia, especially hemodynamically significant arrhythmia. A hemodynamically significant arrhythmia is an arrhythmia that makes the heart unable to efficiently pump blood. Examples of hemodynamically significant arrhythmias include high-grade atrioventricular block, symptomatic arrhythmias in the presence of underlying heart disease, and supraventricular arrhythmia with an uncontrolled ventricular rate.

High-grade atrioventricular block occurs when the atrioventricular (AV) node is unable to send impulses to the ventricles. If the interpretation module 58 detects a high-grade atrioventricular block, the interpretation module 58 assigns a statement number 174 to the ECG designating high-grade atrioventricular block.

Symptomatic arrhythmias in the presence of underlying heart disease are considered a clinical predictor of major cardiovascular risk. If the interpretation module 58 detects arrhythmias in the presence of heart disease, the interpretation module 58 assigns a statement number 174 to the ECG designating the specific arrhythmia and the presence of heart disease.

Supraventricular arrhythmias, especially atrial flutter with uncontrolled ventricular rate, are diagnostic statements of major cardiovascular risk. By way of example only, if the interpretation module 58 detects a rapid response to atrial flutter, the interpretation module 58 assigns a statement number 174 to the ECG designating atrial flutter with an uncontrolled ventricular rate.

Once the interpretation module 58 has analyzed the ECG for diagnostic statements 178 of major cardiovascular risk, the interpretation module 58 analyzes the ECG for diagnostic statements 178 of intermediate cardiovascular risk. One diagnostic statement 178 associated with intermediate cardiovascular risk is prior myocardial infarction. The interpretation module 58 detects prior myocardial infarction in generally the same manner as described above for Q-wave myocardial infarction, although no ST elevation is evident in the ECG.

Once the interpretation module 58 has analyzed the ECG for diagnostic statements 178 of intermediate cardiovascular risk, the interpretation module 58 analyzes the ECG for diagnostic statements 178 of minor cardiovascular risk. Diagnostic statements 178 associated with minor cardiovascular risk include abnormalities in the ECG, such as left ventricular hypertrophy (LVH), left bundle branch block (LBBB), ST/T segment abnormalities that do not affect functional capacity, and rhythms other than sinus rhythm.

Once the interpretation module 58 analyzes the ECG for diagnostic statements 178 of minor cardiovascular risk, the interpretation module 58 performs a serial comparison between the patient's current ECG and the patient's previous ECG, if one is available. The interpretation module 58 performs a serial comparison between the patient's current ECG and the patient's previous ECG in order to determine if the diagnostic statements 178 associated with minor cardiovascular risk are new, i.e. if the diagnostic statements 178 associated with minor cardiovascular risk were not detected in the previous ECG, but have been detected in the current ECG. If the diagnostic statements 178 detected are new, the probability of cardiovascular risk 180 may actually be intermediate or even high. If the diagnostic statements 178 not new, the probability of cardiovascular risk 180 is minor.

Serial comparison between a current ECG and a previous ECG is a method commonly known in the art. Preferably, the serial comparison is performed in the manner described below. The patient's previous ECG, including previously determined statement codes, measurements, and waveforms, is stored in the database of physiological data records 70. The interpretation module 58 performs the serial comparison between the current ECG and the previous ECG. Depending on the cardiac condition being detected by the interpretation module 58, the interpretation module 58 uses at least one of the statement codes, measurements, and waveforms to compare the previous ECG to the current ECG. For example, when the interpretation module 58 is detecting abnormal rhythms, the interpretation module 58 compares the statement codes 170 of the previous ECG to the statement codes 170 of the current ECG. When the interpretation module 58 is detecting changes in the QRS complex, the interpretation module 58 compares the statement codes 170, measurements, and waveforms of the previous ECG to the statement codes 170, measurements, and waveforms of the current ECG. When the interpretation module 58 is detecting ST/T segment abnormalities, the interpretation module 58 compares the waveforms of the previous ECG to the waveforms of the current ECG. In this manner, the interpretation module 58 detects any new diagnostic statements of cardiovascular risk 178 and assigns statement codes 170 to the current ECG designating the new diagnostic statements of cardiovascular risk 178.

It should be understood that the grouping of the diagnostic statements of cardiovascular risk 178 into major, intermediate, and minor probabilities of cardiovascular risk 180 is a statement code 170 setting that can be configured for different clinical settings. For example, a certain arrhythmia may be associated with a major probability of cardiovascular risk 178 in a perioperative setting. However, the same arrhythmia may only be associated with an intermediate probability of cardiovascular risk 178 in a family practice setting during a general cardiovascular screening.

Referring to FIGS. 2 and 7, once the interpretation module 58 assigns one or more statement numbers 174 to the current ECG in the manner described above, the statement numbers 174 are exported from the interpretation module 58 to the processor 44. The processor 44 accesses the statement library 172 in the library of physiological data records 70 in order to correlate the statement numbers 174 with the statement codes 170. Once the correlation between statement numbers 174 and statement codes 170 is made, the processor 44 has access to the textual statement describing the diagnostic statement 178 and to the associated probability of risk 180. The processor 44 then generates a textual report including the diagnostic statement of risk 178 and the probability of risk 180. The generated report may also include a statement suggesting that the clinician consult a cardiologist regarding the interpretation of the ECG. The generated report is then displayed to the clinician on display 42.

FIGS. 8 and 9 are a flow chart illustrating the method of the invention. Referring to FIGS. 2, 7, and 8, the clinician first conducts 190 a patient history. The clinician prepares a patient history by interviewing the patient and asking a series of cardiovascular health-related questions. Specifically, the clinician asks if the patient has suffered from any serious cardiac conditions, such as prior angina, recent or past MI, congestive heart failure, or symptomatic arrhythmias. If the patient history reveals 192 that the patient has suffered from a serious cardiac condition, the clinician preferably consults 194 a cardiologist before the non-cardiac surgery is performed.

If the patient history does not reveal 192 any serious cardiac conditions, the clinician conducts 196 a physical examination. During the physical examination, the clinician determines whether the patient is suffering from serious cardiac conditions such as stable or unstable angina pectoris and compensated or decompensated congestive heart failure. In addition, the clinician determines whether the patient is suffering from any severe valvular diseases, such as stenotic lesions or regurgitant valve disease. If the patient examination reveals 197 that the patient has suffered from a serious cardiac condition, the clinician preferably consults 198 a cardiologist before the non-cardiac surgery is performed.

If the patient history does not reveal 192 any serious cardiac conditions and if the physical examination reveals 197 that the patient has good cardiac functional capacity, the patient is initially designated 200 as having low cardiovascular risk.

Again, if the clinician discovers that the patient has suffered from a serious cardiac condition or the patient has poor functional capacity, preferably the clinician consults a cardiologist before proceeding with the non-cardiac surgery. However, if the patient is initially designated 200 as having a low cardiovascular risk, the clinician acquires 202 the patient's ECG with the acquisition unit 40. The acquisition unit 40 transmits 204 the ECG to the interpretation module 58 for analysis. The interpretation module 58 analyzes the ECG and assigns a statement number 174 to the ECG. The interpretation module 58 then performs 205 a serial comparison by comparing the current ECG with the patient's previous ECG. The interpretation module 58 assigns 205 additional statement numbers 174 to the current ECG designating the results of the serial comparison. The statement numbers 174 are exported 206 from the interpretation module 58 back to the acquisition unit 40 and the processor 44.

Referring to FIGS. 2, 7, and 9, the statement code library 172 is provided 208 within the library of physiological data records 70. The library 70 is coupled to the processor 44 within the acquisition unit and display unit 38. The processor 44 accesses the statement code library 172 and compares 210 the statement numbers 174 generated by the interpretation module 58 with the list of statement codes 170 in order to determine the diagnostic statement of cardiovascular risk 178 and the probability of risk 180 associated with the statement number 174.

Once the statement number 174 is correlated with the statement code 170, the processor 44 first determines 212 whether the statement code 170 includes a probability of cardiovascular risk 180 that is considered major. If the probability of cardiovascular risk 180 is major, the processor 44 generates 214 a textual report including an indicator of major cardiovascular risk and a suggestion to consult a cardiologist. The textual report is displayed 216 to the clinician on display 42.

After the clinician views the textual report suggesting consultation with a cardiologist, the clinician can choose to immediately consult a cardiologist located at an expert location 80. If the clinician chooses to consult a cardiologist, the communication module 60 of the acquisition unit 40 generates and sends 234 an email message including the current ECG to a cardiologist in an expert location 80. The communication module 60 sets 236 a timer with a predetermined time period during which the cardiologist must complete the interpretation of the ECG and send a response. The cardiologist interprets the ECG, generates a textual report of the ECG interpretation, and sends the generated textual report to the acquisition unit 40 via email. The email message including the textual report of the ECG interpretation is received 238 and processed by the acquisition unit 40. The textual report of the ECG interpretation is displayed 240 on display 42. Although the communication between the cardiologist and the acquisition unit 40 is described as email messages, the communication may be any analog or digital form of communication, including telephone calls, intranet messages, or any type of internet messages.

Rather than choosing to consult a cardiologist, the clinician may choose to use the library of physiological data records 70 or the supplemental educational materials 76 to assist in interpreting the ECG.

If the probability of cardiovascular risk 180 is not major, the processor 44 next determines 218 whether the statement code 170 includes a probability of cardiovascular risk 180 that is considered intermediate. If the probability of cardiovascular risk 180 is intermediate, the processor 44 generates 220 a textual report including an indicator of intermediate cardiovascular risk and a suggestion to consult a cardiologist. The textual report is displayed 222 to the clinician on display 42. After the clinician views the textual report suggesting consultation with a cardiologist, the clinician can choose to consult a cardiologist located at an expert location 80, or the clinician can choose to use the library of physiological data records 70 or the supplemental educational materials 76 to assist in interpreting the ECG.

If the probability of cardiovascular risk 180 is not major or intermediate, the processor 44 finally determines 224 whether the statement code 170 includes a probability of cardiovascular risk 180 that is considered minor. If the probability of cardiovascular risk 180 is minor, the processor 44 generates 230 a textual report including an indicator of minor cardiovascular risk. The textual report is displayed 232 to the clinician on display 42. If the statement codes do not indicate even a minor probability of cardiovascular risk, the processor 44 generates 226 a textual report indicating that the ECG is normal. The textual report is displayed 228 to the clinician on display 42.

Various features and advantages of the invention are set forth in the following claims.

What is claimed:

1. A method of assessing a patient's cardiovascular risk, the method comprising the acts of:
   acquiring an electrocardiogram for the patient;
   assigning a first diagnostic statement of minor cardiovascular risk to the acquired electrocardiogram if the acquired electrocardiogram exhibits a non-life-threatening cardiac condition;
   performing a serial comparison between the acquired electrocardiogram and a previous electrocardiogram;
   determining whether the non-life-threatening cardiac condition exhibited in the acquired electrocardiogram was exhibited in the previous electrocardiogram;
   assigning a second diagnostic statement of major cardiovascular risk to the acquired electrocardiogram if the cardiac condition was not exhibited in the previous electrocardiogram;
   determining a probability of cardiovascular risk value based on the second diagnostic statement; and
   displaying the probability of cardiovascular risk value to a clinician.

2. The method of claim 1 and further comprising the act of conducting a patient history and physical examination before the act of acquiring an electrocardiogram for the patient.

3. The method of claim 1 and further comprising the act of inputting the acquired electrocardiogram into an interpretation module and exporting the first and second diagnostic statements of from the interpretation module.

4. The method of claim 1 and further comprising assigning a diagnostic statement of major cardiovascular risk if the acquired electrocardiogram exhibits is at least one of atrioventricular block, symptomatic arrhythmia in the presence of underlying heart disease, and supraventricular arrhythmia with uncontrolled ventricular rate.

5. The method of claim 1 and further comprising assigning a diagnostic statement of intermediate cardiovascular risk if the acquired electrocardiogram exhibits prior myocardial infarction.

6. The method of claim 1 and further comprising assigning a diagnostic statement of minor cardiovascular risk if the acquired electrocardiogram exhibits at least one of left ventricular hypertrophy, left bundle branch block, ST abnormality in the presence of adequate functional capacity, and a rhythm other than sinus rhythm.

7. The method of claim 1 and further comprises and further comprising the act of displaying an indicator of either major, intermediate, or minor cardiovascular risk.

8. The method of claim 1 and further comprising the act of displaying a suggestion to consult a cardiologist.

9. A device for assessing a patient's cardiovascular risk, the device comprising:
   an acquisition unit for acquiring an electrocardiogram;
   a processor coupled to the acquisition unit for
     assigning a first diagnostic statement of minor cardiovascular risk to the acquired electrocardiogram if the acquired electrocardiogram exhibits a non-life-threatening cardiac condition;

performing a serial comparison between the acquired electrocardiogram and a previous electrocardiogram;

determining whether the non-life-threatening cardiac condition exhibited in the acquired electrocardiogram was exhibited in the previous electrocardiogram;

assigning a second diagnostic statement of major cardiovascular to the acquired electrocardiogram if the cardiac condition was not exhibited in the previous electrocardiogram, and determining a probability of cardiovascular risk value based on the second diagnostic statement; and a display for indicating to a clinician the probability of cardiovascular risk value.

10. The device of claim 9 and further comprising an interpretation module coupled to the processor wherein the acquired electrocardiogram is inputted into the interpretation module and the first and second diagnostic statements are exported from the interpretation module.

11. The device of claim 9 wherein the probability of cardiovascular risk value is one of major, intermediate, and minor.

12. The device of claim 11 wherein the processor assigns a diagnostic statement of major cardiovascular risk if the acquired electrocardiogram exhibits at least one of atrioventricular block, symptomatic arrhythmias in the presence of underlying heart disease, and supraventricular arrhythmias with uncontrolled ventricular rate.

13. The device of claim 11 wherein the processor assigns a diagnostic statement of intermediate cardiovascular risk if the acquired electrocardiogram exhibits prior myocardial infarction.

14. The device of claim 11 wherein the processor assigns a diagnostic statement of minor cardiovascular risk if the acquired electrocardiogram exhibits at least one of left ventricular hypertrophy, left bundle branch block, ST abnormality in the presence of adequate functional capacity, and a rhythm other than sinus rhythm.

15. The device of claim 9 wherein the processor generates a textual report and the display indicates the textual report to a clinician.

16. The device of claim 15 wherein the generated report includes an indicator of either a major, intermediate or minor cardiovascular risk.

17. The device of claim 15 wherein the generated report may include a suggestion to consult a cardiologist.

* * * * *

UNITED STATES PATENT AND TRADEMARK OFFICE
CERTIFICATE OF CORRECTION

PATENT NO.    : 6,665,559 B2                                          Page 1 of 1
DATED         : December 16, 2003
INVENTOR(S)   : G. Ian Rowlandson It is certified that error appears in the above-identified patent and that said Letters Patent is hereby corrected as shown below:

Column 10,
Line 40, delete the word "of"
Line 43, delete the word "is"
Line 57, delete the words "further comprises"

Signed and Sealed this

Thirtieth Day of March, 2004

JON W. DUDAS
*Acting Director of the United States Patent and Trademark Office*